United States Patent
Tayebi et al.

(10) Patent No.: US 6,645,769 B2
(45) Date of Patent: Nov. 11, 2003

(54) RESERVOIR MONITORING

(75) Inventors: Davoud Tayebi, Trondheim (NO); Lars Kilaas, Trondheim (NO); Are Lund, Trondheim (NO); Arne Lund Kvernheim, Nesoddtangen (NO); Odd Ivar Eriksen, Olso (NO); Jostein Sveen, Trondheim (NO); Ole Bernt Lile, Trondheim (NO); Marit Valeur Ramstad, Trondheim (NO); Ole Widar Saastad, Olso (NO)

(73) Assignee: Sinvent AS, Trondheim (NO)

( * ) Notice: Subject to any disclaimer, the term of this patent is extended or adjusted under 35 U.S.C. 154(b) by 370 days.

(21) Appl. No.: 09/725,042

(22) Filed: Nov. 29, 2000

(65) Prior Publication Data

US 2001/0036667 A1 Nov. 1, 2001

(30) Foreign Application Priority Data

Apr. 26, 2000 (NO) .............................................. 002137

(51) Int. Cl.⁷ .......................... E21B 47/00; G01N 37/00
(52) U.S. Cl. .......................... 436/56; 436/27; 507/203; 507/277; 166/246; 166/250.01; 166/250.12; 435/29; 435/30
(58) Field of Search ...................... 436/56, 27; 507/203, 507/277, 907; 166/246, 250.01, 250.12; 435/29, 30

(56) References Cited

U.S. PATENT DOCUMENTS

| | | | |
|---|---|---|---|
| 3,508,875 A | * | 4/1970 | Sandiford ..................... 436/25 |
| 3,964,294 A | * | 6/1976 | Shair et al. ................. 73/61.52 |
| 3,991,827 A | | 11/1976 | Schall |
| 4,008,763 A | | 2/1977 | Lowe, Jr. |
| 4,055,399 A | * | 10/1977 | Parrish ......................... 436/27 |
| 4,264,329 A | | 4/1981 | Beckett |
| 4,420,565 A | | 12/1983 | Schmitt |
| 4,520,109 A | * | 5/1985 | Simmonds et al. ........... 436/56 |
| 4,555,489 A | | 11/1985 | Schmitt |
| 4,861,986 A | | 8/1989 | Arnold |
| 5,077,471 A | | 12/1991 | Smith, Jr. et al. |

(List continued on next page.)

FOREIGN PATENT DOCUMENTS

WO 97/44567 11/1997

*Primary Examiner*—Jill Warden
*Assistant Examiner*—Monique T. Cole
(74) *Attorney, Agent, or Firm*—Wenderoth, Lind & Ponack, L.L.P.

(57) ABSTRACT

A method for monitoring hydrocarbon and water production from different production zones/sections in a hydrocarbon reservoir and/or injection wells and detection of different phenomena such as e.g. local variations in pH, salinity, hydrocarbon composition, temperature, pressure, microorganisms, and the difference between production of formation and/or injection water from various zones/sections. The method includes dividing regions around wells in the reservoir into a number of zones/sections, and injecting or placing specific tracers with unique characteristics for each zone/section into the formation in these regions such that tracers are placed as integrated parts of the well completion or placed and immobilized in these regions through injection, squeeze or by other techniques. The tracers can also be immobilized or placed on a filter, a casing or other constructions surrounding the well in each zone/section. The tracers are specific or introduced to give specific information from each zone/section. The method further includes chemically immobilizing or integrating the tracers in the formation or constructions or filters around the wells, the tracers (tracer carriers) being chemically intelligent and released as a function of specific events, and detecting the tracers downstream providing information about the various zones/sections. The method may be used in a local alarm system for water breakthrough or for improved oil and gas recovery (IOR) in horizontal production and injection wells.

15 Claims, 9 Drawing Sheets

U.S. PATENT DOCUMENTS 5,212,093 A * 5/1993 Richardson et al. .......... 436/27
5,284,663 A * 2/1994 Speaker ...................... 424/489
5,723,781 A    3/1998 Pruett et al.
5,881,807 A    3/1999 Bøe et al.
5,892,147 A    4/1999 Garnes et al.
6,003,365 A * 12/1999 Pope et al. .............. 73/152.39
6,214,624 B1 * 4/2001 Barker et al. .................. 436/8

* cited by examiner

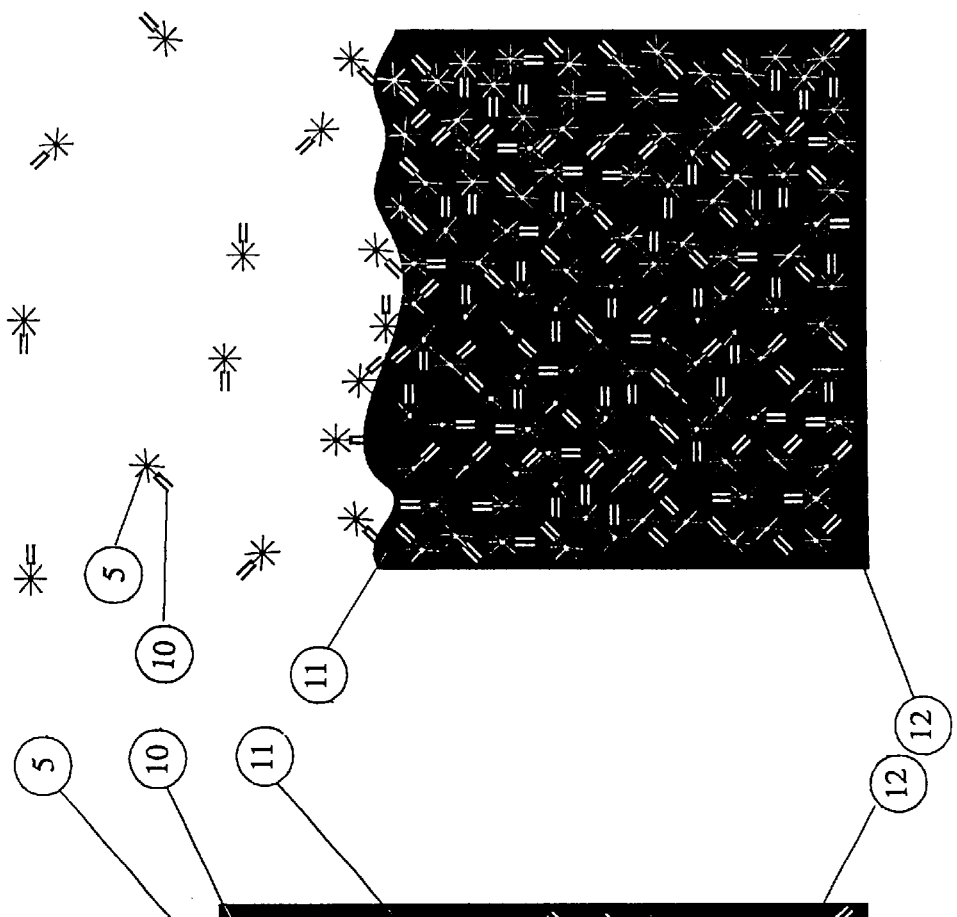
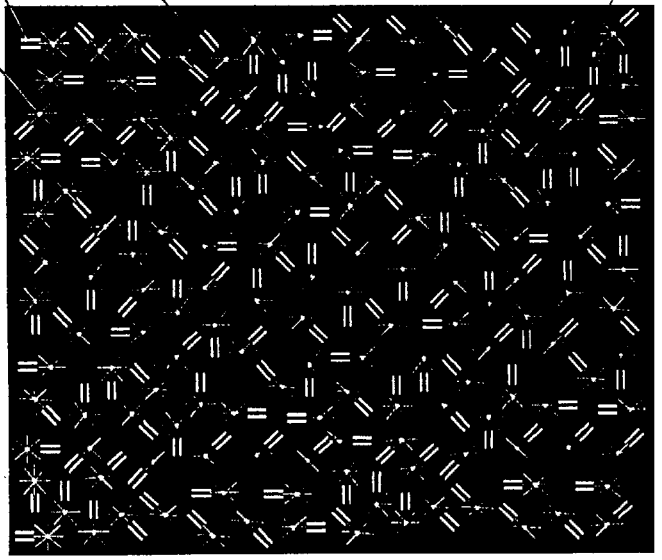

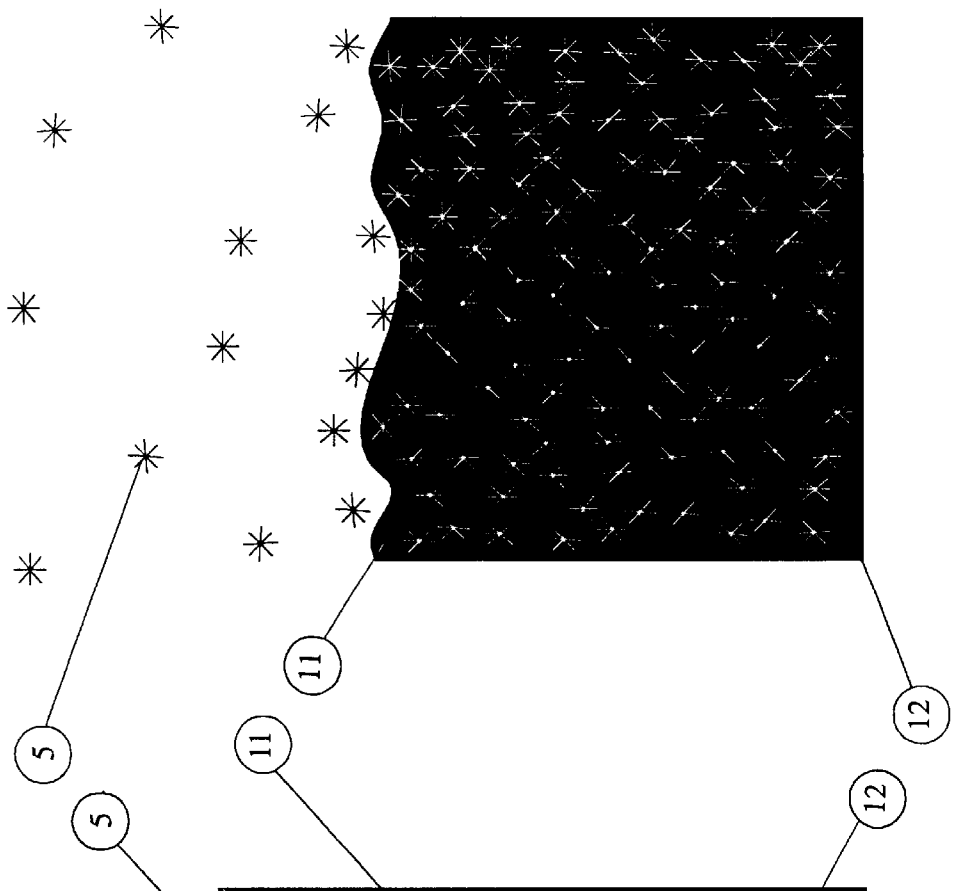
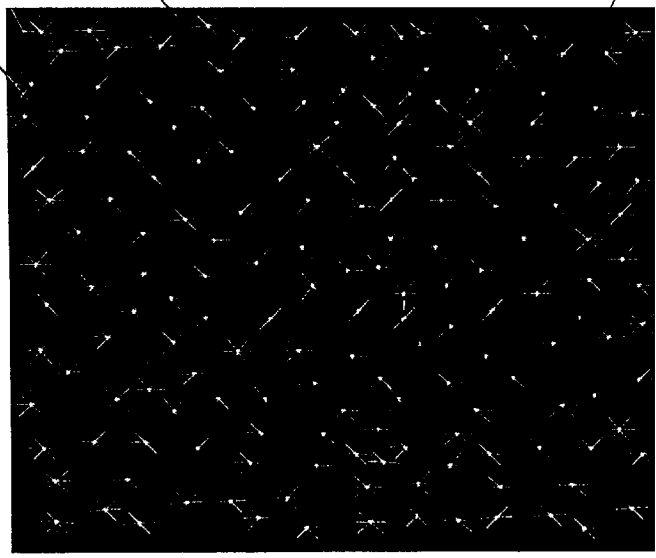
Figure 5(A)
Figure 5(B)

RESERVOIR MONITORING

BACKGROUND OF THE INVENTION

1. Field of the Invention

The present application relates to a method for monitoring the hydrocarbon and water production from different production zones/sections in a hydrocarbon reservoir and detection of different phenomena such as e.g. local variations in pH, salinity, hydrocarbon composition, temperature, pressure, microorganisms, and the difference between production of formation and/or injection water from various zones/sections in wells in a hydrocarbon reservoir. The method enables both short time and long time monitoring and detection of the above mentioned phenomena. Uses of the invention are also disclosed.

2. Description of Related Art

A geological porous and permeable formation in the ground containing hydrocarbons is called a hydrocarbon reservoir. A hydrocarbon reservoir rock type consists of two elements, the matrix, which are the solid rock fragments, and the pore volume in between the rock fragments. The pore volume constitutes the porosity, $\phi$, which is the fraction of pore volumes relative to the total volume which is set equal to 1.0. For example, $\phi=0.3$ means that 30% of the total volume is pore volume and the rest of the volume (70%) is the rock matrix.

In a hydrocarbon reservoir the pore volume is generally filled with water, oil and/or gas. Due to density differences, the hydrocarbons will accumulate in the upper part of the reservoir. Water will occupy the pore spaces below the hydrocarbon zone in the reservoir. Between the hydrocarbon zone and the water zone below (the aquifer), there is a transition zone where the hydrocarbon saturation drops from close to 100% down to 0%, representing the Oil-Water-Contact, OWC.

During the production of hydrocarbons, water is normally displacing the hydrocarbon and the OWC level will rise in the reservoir. After some period of production, the water fraction of the produced fluids will increase. Generally, the fraction of water in the total volume of produced fluids increases steadily. Finally, the water fraction will be too high and the production becomes non-profitable. Often the production may come from different layers or zones of the formation cut by the well. The individual zones may have different permeability and will normally behave differently during production. It is generally an advantage to know this behavior. The gathering and analyses of information from the reservoirs during the production is called Reservoir Monitoring. The typical types of collected data are temperature, pressure, electrical resistivity, and water saturation in the reservoir close to the production well. Other types of information may be seismic maps of the whole reservoir at different stages of the hydrocarbon production.

When hydrocarbons are produced from a porous and permeable geological formation in the ground, a reservoir, the flow of hydrocarbons and water can come from different zones or layers of the reservoir. To monitor and analyze the production of different fluids, it is often important to get information about the type of fluids and the amount of the various components that flow from each zone.

A known method of examining the local flow properties in an oil and/or gas producing well is to lower a logging tool into the well. This is described e.g. in U.S. Pat. Nos. 4,861,986, 5,723,781 and 5,881,807.

To examine the local production the logging equipment lowered into the well measures the amount of oil and/or gas flowing in the well at different places along the well. Using this technique it is possible to calculate the amount of oil flowing into any region of the well. Among the disadvantages of this technique is that the production of oil and/or gas has to be wholly or partially stopped during the logging. This is a major disadvantage since one wishes to measure the local amount of oil and/or gas flowing in the well during the logging. Using this technique, it is often difficult to distinguish between the amount of oil and water in a mix flow. For a long horizontal borehole (4–6 km) it is very difficult or almost impossible to use the technique since special leading equipment is required to insert the logging probe into the horizontal wells. Furthermore, putting logging equipment into a well reduces the cross-sectional area of the producing well, resulting in a larger pressure drop. The method is also very expensive.

Another known technique in reservoir study is the application of traceable materials. Tracers are used to determine size and shape of reservoirs. U.S. Pat. Nos. 4,420,565 and 4,264,329 describe methods for following fluid flow in underground reservoirs using tracer materials. In U.S. Pat. No. 4,420,565 the depth of recovery is determined by injecting a solution containing a small amount of one or more water-soluble tracer compounds into the formation at a predetermined depth from the injection system and recovering it in the production system. The tracer compounds are then identified using gas chromatography and a flame ionization detector. U.S. Pat. No. 4,264,329 uses metal chelates as tracers, and liquid chromatography and fluorescence spectroscopy to detect the metal chelates in the produced fluid.

U.S. Pat. Nos. 3,991,827 and 4,008,763 describe a method for determination of solid particle leakage into the wellbore from different solid particle packs placed along the well using tracer particles. High concentration (50–70% by weight) of tracer particles are packed in a plurality of solid particle packs which are placed in a well to prevent solid production from the formation into the wellbore. The tracer particles used are unique for each particular pack, for example particles with different colors. If any of the solid packs is leaking during the production, the tracer particles from that pack or packs will follow the produced fluid that is analyzed at the surface to determine which pack is leaking solid particles. Using this technique, subsequent workover of the well can be limited to the pack or packs where the leaking packs are identified, rather than being directed to the whole well.

The technique described in U.S. Pat. Nos. 3,991,827 and 4,008,763 is a method for short time detection of leaking packages. Very high concentrations of tracer particles (50–70% by weight) are being used, where tracer particles are mixed with the packing particles and placed in packs around the well. There is no chemical connection between tracer particles and packing materials. The tracers will follow the flow regardless of the fluid type. The packs leaking particles will lose a large amount of tracers in a short time and therefore are not suitable for long time monitoring. In addition, migration of a large amount of solid particles such as sand and fines can wear out pipes, valves and other equipment. On the other hand, the tracers will be captured in the packs that do not leak, and therefore no information will be available from those regions. The method as it is described is useable only for examining the solid particle leakage.

U.S. Pat. No. 5,892,147 describes a procedure for determination of oil and/or gas inflow from a reservoir into a wellbore. Different radioactive isotopes are used as tracers placed in different zones along the well. The radioactive isotopes are fixed either on the outside of the transport pipe or inserted into the formation through the well casing using perforation guns. Based on the amount of the measured tracers the amount of oil and/or gas flowing into the well at each zone is calculated.

In both cases described in U.S. Pat. No. 5,892,147, the radioactive isotopes are withdrawn by the fluid as a result of the fluid flow, where the fluid could be oil, water or gas. Based on this technique it is therefore difficult to judge which zone is producing what. Fixing the radioactive isotopes on a surface of a transport pipe is limited only to those wells having a transport pipe with the arrangements required for this technique. In the other alternative the radioactive isotope particles are inserted into the formation as a load to an explosive charge which is shot through the well casing. The tracers are washed out with the first batches of fluid flow through the perforation holes since they mostly lie free on the interior surface of the perforation holes without any chemical connection to the formation. This method therefore gives some information about the initial phase of the production in each zone. In addition, the application of radioactive isotopes as tracers is expensive and requires special handling.

SUMMARY OF THE INVENTION

The present invention has been conceived to solve or at least alleviate the problems of the prior art as described above. Thus, in accordance with the present invention there is provided a method for monitoring and detection such as stated in the introduction. The method of the invention comprises dividing regions around wells in the reservoir into a number of zones/sections, and injecting or placing specific tracers with unique characteristics for each zone/section into the formation in these regions such that tracers are placed as integrated parts of the well completion or placed and immobilized in these regions through injection, squeeze or by other techniques, or the tracers can be immobilized or placed on a filter, a casing or constructions surrounding the well in each zone/section, the tracers being specific or introduced to give specific information from each zone/section, and the method is characterized in chemically immobilizing/integrating the tracers in the formation or constructions/filters around the wells, the tracers (tracer carriers) being chemically intelligent and released as a function of specific events, and detecting the tracers downstream providing information about the various zones/sections.

The regions around wells in a reservoir are divided into a number of zones/sections, and specific tracers with unique characteristics for each zone/section are placed as integrated parts of the well completion. The tracers are chemically immobilized or integrated into the formation or in/on the constructions/filters around the wells. The tracers and/or tracer carriers are chemically intelligent and released as a function of specific events. Tracers are detected downstream somewhere along the production line or on the surface, providing information about the various zones/sections in the reservoir.

Among the many advantages of the present invention is the determination of local and detailed information about the above mentioned phenomena, using a fluid intelligent tracer technique together with a relatively simple data detection system which requires no equipment down-hole during production. Therefore the well hole remains unchanged resulting in a lower pressure drop. Since there is no equipment down-hole, there is no need for equipment maintenance either. The method gives both short time and long time information which can be used, for example, for early warning, start phase detection, or long time monitoring, etc. The method uses no radioactive isotopes, or any material that is harmful to the environment.

The present invention provides a fluid intelligent and reliable tracer technique for short time and long time monitoring of different production zones/sections in oil and gas production wells and also for detection or early warning of phenomena such as water breakthrough, local variations in pH, salinity, hydrocarbon composition, temperature, pressure and microorganisms. The method enables also measurement of the difference between production of formation and/or injection water from various zones/sections in a hydrocarbon reservoir. The main advantage of this invention is that it makes it possible to collect the local detailed information from each individual zone of the reservoir, and production and/or injection wells using a fluid intelligent tracer technique. The well or wells in a reservoir are divided into a certain number of separate zones/sections equipped with proper tracers of unique characteristics for each zone/section as illustrated in FIG. 1. The tracers are placed as integrated parts of the well completion chemically immobilized or integrated into the formation and/or in/on the constructions or filters around the wells. The tracers can also be placed in small chemically intelligent packages located around the well in the reservoir and/or in the constructions or filters around the wells (FIGS. 2–8). The tracers can be immobilized or placed on the filter or the casing around the well in each zone/section. The tracers and/or tracer carriers are chemically intelligent and released as a function of specific events. Tracers are detected downstream somewhere along the production line or on the surface. The collected information can be used to study the local flow conditions in each zone/section and to describe the reservoir behavior during production. Such information includes for example production rate, location and the type of produced fluids, e.g. how much oil, water or gas is produced and from where in the reservoir they come. The method can be used to study the reservoir dynamics behavior in the neighborhood of the production and injection wells. The method can be used to detect the phenomena such as water breakthrough, variations in pH, salinity, hydrocarbon composition, temperature, pressure and microorganisms in each well section/zone. Using intelligent tracers it is also possible to distinguish between produced injection water and formation water from each zone/section. The technique can be also used as a local alarm- or early warning system for both quantitative and qualitative detection of the appearance of phenomena such as water breakthrough, variations in pH, salinity, hydrocarbon composition, temperature, pressure, and microorganisms. The invention can in principle also be used for other production processes and fluid transport facilities.

BRIEF DESCRIPTION OF DRAWINGS

The above and further advantages may be more fully understood by referring to the following description and accompanying drawings of which:

FIG. 4(A) schematically illustrates a number of tracers (5) being packed/immobilized into a small package (12), e.g. a chemically intelligent gel or a polymer package (11). The tracers (5) are chemically connected to the packing material (11) by link (or other types of weak forces) (10). The package (12) may have any shape or size e.g. such as small capsules, tablets, polymer particles or polymer matrixes.

FIG. 4(B) illustrates schematically the gradually release of tracers (5) from the package (12) as a result of a chemical reaction leading to de-gradation of the packing material (11) and breakage of the link (10).

FIG. 5(A) schematically illustrates a number of tracers (5) being packed/immobilized into a small package (12), e.g. a chemically intelligent gel or a polymer package (11). The package (12) may have any shape or size e.g. such as small capsules, tablets, polymer particles or polymer matrixes.

FIG. 5(B) illustrates schematically the gradually release of tracers (5) from the package (12) as a result of a chemical reaction leading to degradation of the packing material (11).

The release process for tracers in all the above mentioned methods could be as those illustrated in FIGS. 2–5 or any of their combinations.

Figure 9:
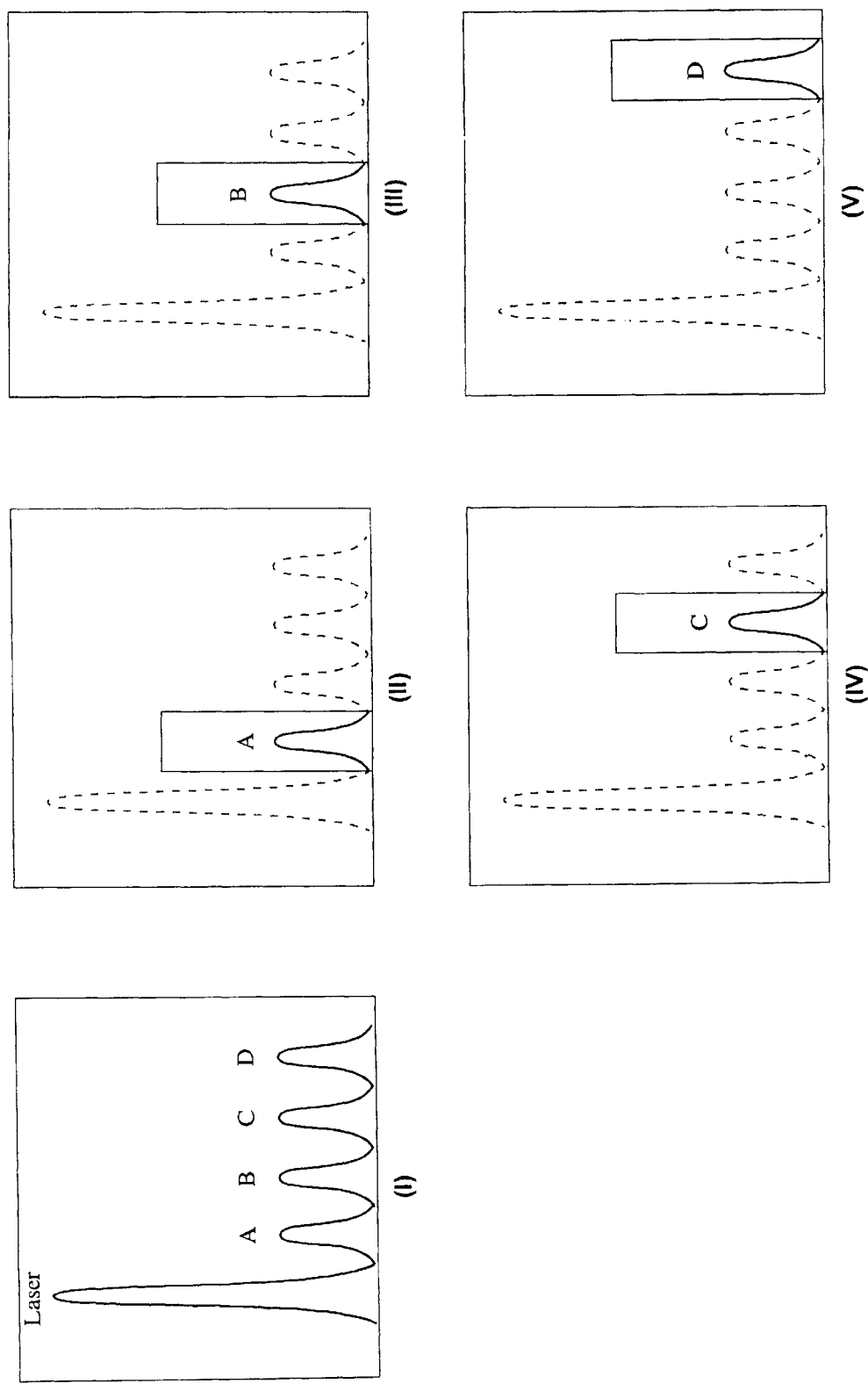

FIG. 9 is a schematic illustration of the method for selection of the desired light spectra for detection of individual tracer particles with different emission wavelength using optical filters. (I): Hole spectra of the reflected and emitted lights from the carrying fluid and tracer particles respectively. (II), (III), (IV) and (V): Blockage of the unwanted light spectra and transmission of the desired light spectra using proper optical filters.

DETAILED DESCRIPTION OF THE INVENTION

A series of various traceable materials such as tracer particles, biologically coded materials, design chemicals or fluids can be placed in different known locations, zones or sections in a reservoir along a well or through the injection wells. It is also possible to use specific reservoir microorganisms or rare minerals as tracers. The tracer materials will be chemically immobilized in the reservoir formation along the well, or packed in the fluid intelligent packages using special chemical compounds placed along the well. In cases where there is a filter or other constructions around the well, the tracers can be chemically immobilized in or on the construction along the well in separate zones/regions. The tracers are e.g. placed along the well with certain patterns, injected into the constructions or filters around the well, mixed with the material in the filter content, or immobilized or placed on the filter, the casing or constructions surrounding the well in each zone/section. The immobilization of tracers on these constructions can for instance be performed before the insertion of the filter or the casing into the well. In this case one may use different tracers or tracer combinations for each part of the filter or the casing dividing the well into various sections/zones. The tracers will be released gradually as a result of the production of the individual fluids in each specific zone or be triggered/released by specific events like water breakthrough, enzymes or by other mechanisms. The tracer release mechanism could be a degradation process of the matrix holding the tracers by weak forces or degradation of the link or links between tracers and the reservoir formation or packing material (FIGS. 2–8). The released tracers will follow the produced fluids out of the well and can be detected somewhere along the production line downstream. Since the locations of different tracers in the reservoir formation are known in advance, the behavior and the dynamics of the individual production zones (and the event releasing the tracers) along the well can be monitored by detecting the type of tracers coming from different sections.

The tracers are made "chemically fluid intelligent" such that they will be released as a response of specific events, e.g. they respond to an oil flow (oil-active) but show no response to a water flow (water-resistant). Another group of chemical compounds can be placed in the same region, which release tracers in water flow (water-active) but shows no response to an oil flow (oil-resistant). This means that when there is no or very little water production, there will be no release of water-active tracers, and vice versa.

Tracers which are released in the gas-phase of a multiphase system are also possible to construct and monitor. Intelligent chemicals or materials sensitive to specific events such as water breakthrough, local variations in pH, salinity, hydrocarbon composition, temperature, pressure, microorganisms, etc. which release specific tracers can also be placed in the same region. These tracers can be used both as an alarm system (early warning) and for the local study of the specific phenomena over time. Specific chemicals can be placed latent in the formation along the well in the reservoir being unique for each well zone/section. These compounds can be activated to release tracers using specific triggers for example through the injection system. Using this technique for release mechanism combined with the injection water will allow the local detection of for example water breakthrough of the injected water. In such a system produced formation water and/or injected water will be detectable by the release of water-active tracers (compounds sensitive to water which release tracers), but the difference between injection or formation water will be distinguishable using the above mentioned latently stored tracers.

Two or more time dependent tracer release processes (long time release and short time release process) can be designed using different chemical compounds. In a short time release process large amounts of specific tracers are released in a short time, while in the long time release process small amounts of another group of tracers are released gradually over a long time. One or several tracer groups with different release processes and characteristics can be placed in the same region/zone. The purpose of these processes could be different, for example for early warning, for start phase detection, or long time monitoring, etc. Another type of tracer would be the sudden release type. In this case a relatively small amount of tracer can be localized in the well to detect some later event which could occur in that zone (type of fluid, pH, salinity changes, temperature, pressure changes etc.).

The tracers can be e.g. fluorescent, phosphorescent, magnetic particles or fluids, easily detected compounds by chromatographic methods, biologically coded materials or rare minerals which are not usually found in the produced fluids from the concerned reservoir. Tracers responding to acoustic signals may also be possible to construct. The tracers can be injected in the reservoir formation in the neighborhood of the well and fixed in place (immobilized/linked) chemically or physically. Another possibility is to put a compact amount of tracer materials fixed in a fluid intelligent chemical compound in the reservoir formation as a solid package or swellable porous or solid polymer matrixes or particles. In cases where there is a filter or other constructions around the well, the various tracers can also be chemically immobilized in/on the construction along the well in separate zones/regions. The tracers may also be injected into the reservoir through injection wells. The tracers will be released either by e.g. bleeding, degradation of the support matrix/tracer carrier (chemical reaction, displacement like ionic exchange, etc.) when exposed to the activating fluid (e.g. oil or water) or mechanically, for example by being washed out as a soap by the flow of the activating fluid. Thus, the amount of released tracer material will be a function of the local activating fluid flow rate or production rate. The tracers will follow the produced fluids and will be detected somewhere downstream along the production line. Information about the location, type and production rate of the concerned fluids will be a function of the amount and the type of released and measured tracers.

The unique feature of this invention is the confinement of an easy detectable tracer (any kind) in an arrangement where the tracer is released by changes in the local environment of the tracer. The changes in the environment can be changes in the flow, fluid composition, temperature, pressure or other chemical/physical condition. Such changes may even be related to the local micobiology. The tracer is placed in such a way that specific information from sections of a well is obtained when the tracer is released and detected. The tracer may be a chemical substance in itself, be produced as a chemical substance because of an event, a larger macromolecule (DNA, protein sequence etc.), particles or any other entiety which can be easily detected in a water phase, an oil phase, a gas phase or a fluid mixture. The influence of chemicals in the reservoir formation or zones should be insignificant.

Possible detection methods may be based on optical techniques, acoustic, magnetic, capacitance, PCR, and microwaves methods, etc. The proper method depends on the applied tracers and how/where they are released.

EXAMPLES

The examples/cases given are only intended to illustrate some of the possible applications of "intelligent chemicals and microbiology" in wells in a reservoir. These examples must not be used to limit the scope of the inventive idea.

Neither the method for placement of different tracers, the location in the reservoir nor the distance from tracers to the production well are critical for the invented method and must not be regarded as a limit of this invention. Typical methods for placement of tracers in the production well that will be used in the present invention are well known squeeze methods or direct placement in the "sand pack" during the completion of the well.

The tracers can be synthetic and/or natural chemicals, monomeric compounds or polymers which can be detected and give information about their origin (specific zone/section), different flow rates and environmental data (e.g. oil, water, gas, water breakthrough, local variations in pH, salinity, hydrocarbon composition, temperature, pressure, microorganisms, etc.) of the different zones/sections in the reservoir at all times.

The tracers may be detected by different techniques such as optical fibers, spectrophotometric methods, PCR techniques combined with sequential analysis, or by chromatographic methods. The invention is not restricted to the above mentioned techniques.

1. Examples on Behavior and "Delivery" of Tracers 1.1. Tracer Molecules which Are Adsorbed or Covalently Bonded to the Reservoir Formation In the region close to a production well or other suitable places in the reservoir the tracers can be immobilized by adsorption just by injecting a solution containing the tracers. Tracers can also be pre-added to the "sand pack" during the well compilation. By controlling the type and amount of different functional groups in the tracer molecules, one can enhance adsorption to the formation. Attachment to the formation may also be induced by complexing groups such as e.g. carboxylic acids, sulfonic acids, phosphonic acids, phosphates and hydroxy groups. The tracers may be hydrophobic or hydrophilic in order to respond (to be soluble) in water or mineral oils. In this way, the tracers may be tailor-made to give specific information in both aqueous and non-aqueous media. Flow rates for the hydrocarbon, water, and/or gas flow will be essential for the detachment/liberation and concentration of the different tracers in the production stream.

1.2. Tracer Molecules Covalently Linked to Polymers

In order to ensure sufficient attachment of tracers (high concentrations) to the formation, it is preferred to use tracers linked covalently or by ionic interactions to polymers which are specially designed to adhere to the formation. A high degree of functionality, e.g. carboxylic acids, sulfonic acids, phosphonic acids, phosphates and hydroxy groups and co-operative effects, e.g. ionic and hydrogen binding may be introduced in the polymers due to multiple binding sites that enhances binding to the formation. By varying the link between the tracer and the polymer, release mechanism and rate can be controlled. The mechanisms for release of tracers may be as follows:

Release of tracers from the polymer by breaking the "binding" between these moieties regardless of type of binding (hydrophobic, ionic or chemically covalent).

Release of tracer by degradation of the polymer resulting in small oligomers containing tracers (solved) in the production stream. The nature of the oligomers/polymers will influence the solubility of the mentioned fragments, including the tracer, in different media.

A combination of the two methods mentioned above.

1.3. Tracer Molecules Covalently Linked to the Surface of Polymer Particles (Poly or Monosized Particles)/inorganic Particles or Tracers Immobilized/encapsulated in such Particles It is also possible to bind tracers to different organic or inorganic particles (carriers). The "carriers" are placed in different zones/sections, and their size, chemical composition and functionality must not prohibit free flow of oil/ fluids within the reservoir. Some examples of tracer carrier systems are as follows:

Tracers attached to polymers in a network (gel) which are placed in the reservoir formation or in the "sand pack". The polymer system should not block the pores in the formation. Release of the tracers is achieved by breaking the binding between the polymer and tracer and/or by disintegration of the gel itself.

Tracers can be attached to the polymer chains building up the polymer particles, immobilized in the polymer matrix or attached only to the surface of the particles. The invention is however not limited to the use of polymer particles and any type of particle (carrier) may be used. The particles can be placed in the reservoir formation or in the sand pack. The release of tracers is achieved by breaking the binding between the polymer particle (any carrier) and the tracer, and/or by disintegration of the particle itself in such a way that the tracers leaking out from the carrier.

Degradation of the polymer particles (or carriers) may be controlled by the use of specially defined cross-linkers. During manufacturing of the polymer particles (including the introduction of tracers) the cross-linker is stable, but in special environments the cross-linker degrades or swells, and the polymer matrix disintegrates into soluble polymers. The cross-linkers can be modified to be sensitive towards e.g. pH, temperature, water (hydrolysis) or special chemicals added to the zones/sections. It is also possible to use wax systems where the tracers are immobilized in the wax (tablets) and the tracers are released when the oil (oil soluble wax) or water (water soluble wax) comes in contact with the wax tablets.

2. Examples of Immobilization of Different Tracers (Ligands)

Different oligonucleotides with special functional chemical groups at the ends (e.g. carboxylic, hydroxy, thiols) are to day commercially available. These functional groups may be used to chemically couple and/or complexing the oligonucleotides to a carrier like polymer particles or gels. The other unattached ends of the biomolecules can either be used to couple a secondary tracer and/or a substance which gives a certain solubility or compatibility toward different media (oil, water, salinity, pH). E.g., one may use an oligonucleotide with a primary amine group at one end and a thiol group at the other end. The thiol groups are used to chemically bind the biomolecules to secondary molecules using maleimide chemistry (no reaction of amine groups take place) whereas the amine groups are used to bind the new complex molecules to the carrier just by using different pH in the coupling reactions.

Experiments have been performed were oligonucleotides have been immobilized through carboxylic, epoxy, amine and thiol groups onto non-degradable polymer particles (e.g. polystyrene, acrylates) and coupling onto both degradable polymer particles having polyanhydrides, and or polyesters in the polymer matrix. Direct and indirect methods for chemical binding, physical adsorption or ionic interactions are complementary binding methods. In some cases the "free" end of the immobilized biomarker may be coupled to e.g. biotin whereby the whole complex can be isolated using for example super paramagnetic particles (carriers) having streptavidine on the particle surface. This is one of the possible ways of concentrating the samples prior to a PCR amplification, detection and determination. Hybridization techniques may also be used prior to a sequential analysis.

3. Release of Tracer from Water-active Matrix

The production of water from a specific zone in the reservoir formation may be monitored by the invention. One way to do this would be to make a polymeric matrix or particle with a chemical tracer that is released by contact with water at the given conditions, e.g. encapsulation. The chemical tracers may be perfluorinated hydrocarbons such as perfluoro butane (PB), perfluoro methyl cyclopentane (PMCP) or perfluoro methyl cyclohexane (PMCH) that can be detected by mass spectroscopy (MS) or electron capture detection (ECD). Various specific perfluorinated hydrocarbons may be used for the different zones of the formation in order to monitor the water production from these zones. Tracers may also be released by chemical reactions induced by sudden changes in the water phase like pH, ionic strength or heat. Such examples may be degradation of organic anhydrides, esters or amides. The polymers used for encapsulation of the tracers may be commercially available polymers or copolymers that will degrade in water such as poly acrylamide (PAA), poly ethylenglycols (PEG), poly lactic acid (PLA), poly glycolic acid (PGA) and copolymers thereof.

The event of a water breakthrough can be detected if the formation (or a plug located in the formation) releases a detectable tracer when the water or brine passes. One way to do this would be to attach chemically a compound that is released by contact with water at the conditions given. Such chemical may by organic anhydrides. The released component can be detected downstream.

4. Release of Tracer from Hydrocarbon-active Matrix

The production of hydrocarbons from a specific zone of the formation may be monitored by the invention. One way to do this would be to make a polymeric matrix or particle with a chemical tracer that is released by contact with hydrocarbons at the given conditions, e.g. encapsulation. Such chemical tracers may be perfluorinated hydrocarbons such as perfluoro buthane (PB), perfluoro methyl cyclopentane (PMCP) or perfluoro methyl cyclohexane (PMCH) that can be detected by mass spectroscopy (MS) or electron capture detection (ECD). Various specific perfluorinated hydrocarbons may be used for the different zones/sections of the formation in order to monitor the hydrocarbon production in different zones/sections. Tracers may also be released by chemical reactions induced by sudden changes in oil phase pressure, heat or changes in solubility capability (heavy or light petroleum fractions). Particle or polymer swelling may be one of such mechanisms releasing the tracer. The polymers used for encapsulation of the tracers may be commercially available polymers or copolymers that will degrade in hydrocarbons such as poly methyl methacrylates (PMMA), poly methylcrylates, poly ethylenglycols (PEG), poly lactic acid (PLA), poly glycolic acid (PGA) and copolymers thereof.

5. Detection of Reservoir Microorganism

The presence of microorganisms in oil reservoirs may be demonstrated in the produced water by traditional isolation and cultivation techniques. Such methods are quite time-consuming. In offshore oil reservoirs the sulphate reducing bacteria (SRB) are often dominating, and these microorganisms produce $H_2S$ during growth. These organisms are highly unwanted in the produced fluid/oil, because they may cause souring of the reservoir, unwanted plugging of pores in the formation and/or results in corrosions. The activity of SRB's may be demonstrated by measuring the level of $H_2S$ in the produced water.

Growth of microorganisms in reservoirs can be identified by online monitoring using different fluorogenic and/or chromogenic enzyme substrates. The substrates can be covalently bonded or adsorbed to a matrix, e.g. a gel-matrix, a polymer or polymer-particles, which are placed in the reservoir. Microorganisms in the reservoir produce extracellular enzymes (biocatalysts), for example proteases/peptidases and lipases. By using appropriate substrates, these enzymes will catalyze a cleavage of the substrates and the fluorogenic/chromogenic part of the substrates (the tracer part) will be released. The fluorophores/chromophores can be detected online somewhere along the production line downstream. By using different fluorogenic/chromogenic compounds in different localization of the reservoir, information about microbial activity in the different zones/sections can be obtained.

The substrates used in the method of the present invention are generally substrates for extracellular enzymes present in almost all microorganisms, for example lipases and proteases/peptidases. Lipases hydrolyze the ester bond in fats (esters of glycerol's and fatty acids) and esters of two carboxylic acids, and proteases cleave peptide bonds between amino acids in proteins and peptides. The substrates are covalently bond to a matrix in one end and to a fluorogenic/chromogenic compound (the tracer) in the other end. The carboxyl terminus of the end amino acid of a peptide may for example be conjugated to an amine-containing fluorophore (the tracer compound) to create a fluorogenic peptidase substrate. The substrates may be bond to the matrix for example via an amino group in a protein/peptide substrate or a carboxyl group in a fat/triglyceride substrate. The tracer materials can be placed in the reservoir formation as described elsewhere.

6. Detection of Tracers by Optical Methods

One of many possible tracers is to use fluorescent or phosphorescent tracer particles/materials/chemicals. When such particles/materials/chemicals are used as tracers, they can be detected anywhere outside the reservoir along the production line from the well head to the receiving unit on land, ship or platform using for example a fiber optical technique. The on-line detection by optical fibers has many advantages including simple, fast and reliable operation. The optical probe can be made very small and flexible so it can be placed almost anywhere in the production system. FIGS. 1A and 1B show simple schematic illustrations of a horizontal well 1 and a vertical well 2 divided into different zones A, B, C and D (3). The zones A–D are equipped with various tracers with different physical and/or chemical properties such as tracer particles/chemicals with different emission wavelengths. The tracers are placed in known reservoir zones/regions. When the tracers are released, they will follow the main flow toward the receiving unit (not shown in FIGS. 1A and 1B). The concentration and passing frequency of different tracer particles can be detected by using a proper detection technique. The detection assembly (4) can be placed along the main flow direction e.g. on the top of the well, somewhere along the transporting pipeline or even just before the receiving unit.

Local motion of a single particle/chemical in a fluid flow can be determined using optical fibers. This measuring principle can be applied for simultaneous determination of flow properties of various particle groups in a flow using different tracer particles. These tracer particles may have the same physical properties apart from the radiation properties. This can be achieved e.g. by a fluorescent dye impregnation of the tracer particles. It is then possible to distinguish between the radiation from various tracer particles.

Figure 1:
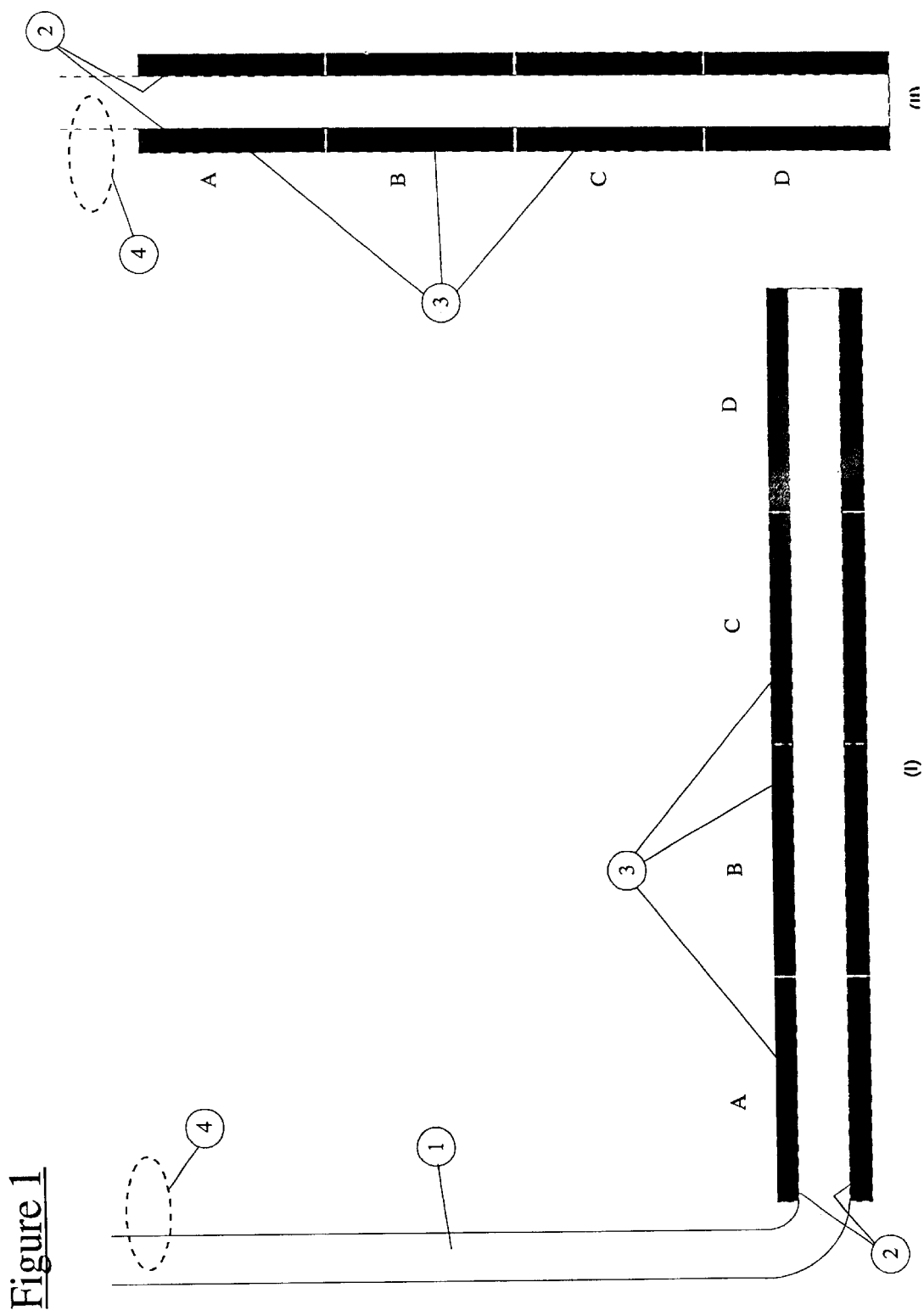
FIG. 1 is a schematic illustration of the horizontal part (I) and/or the vertical part (II) of a well in a reservoir (2) divided into a certain number of zones/sections (3), e.g. A–D according to the invention equipped with specific tracers with unique characteristics for each zone/section.
Figure 2A:
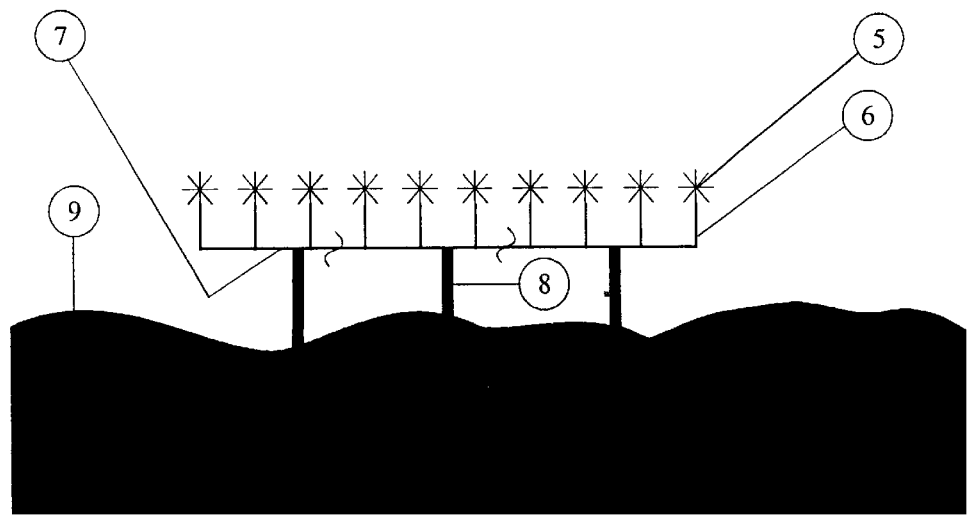
FIG. 2(A) illustrates schematically a number of tracers (5) chemically immobilized (6–8) on e.g. the pore wall of a rock matrix or a polymer matrix, the surface of a sand particle, a polymer particle, an inorganic particle, or on any other compact or porous surface or matrix (9).
Figure 2B:
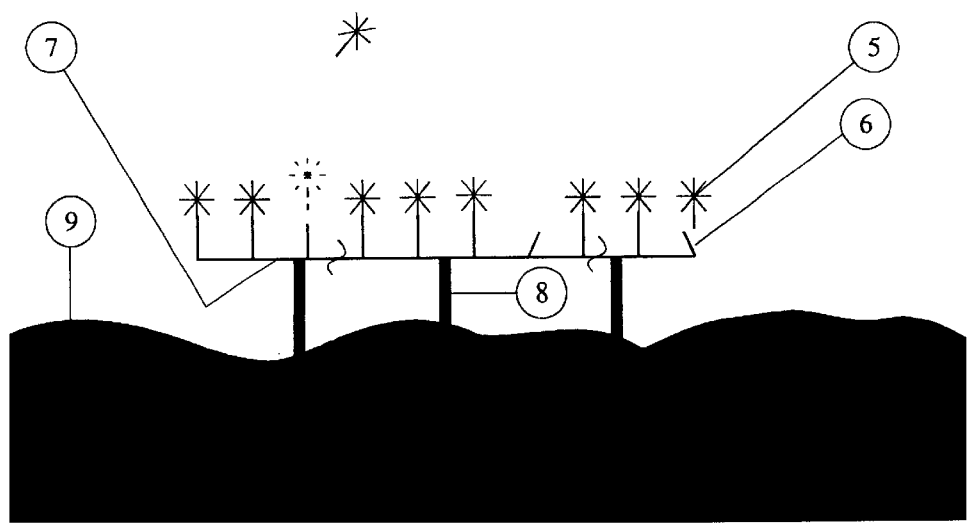
FIG. 2(B) schematically illustrates a tracer (5) being released from the formation (9) as a result of a chemical reaction leading to the breakage of a link (6) between the tracer (5) and a link (7).
Figure 3A:
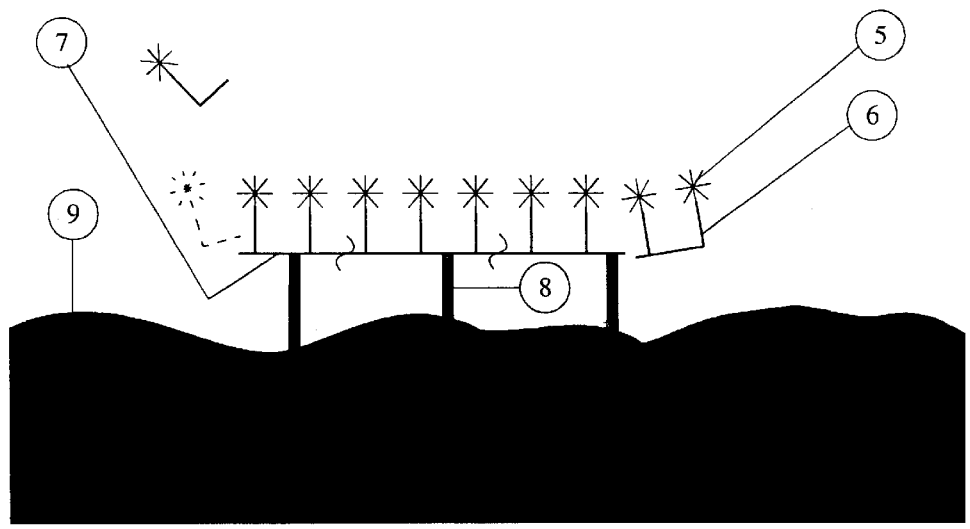
FIG. 3(A) schematically illustrates one or several tracers (5) being released from the formation (9) as a result of a chemical reaction leading to the breakage of link (7) between the link (6) and link (8).
Figure 3B:
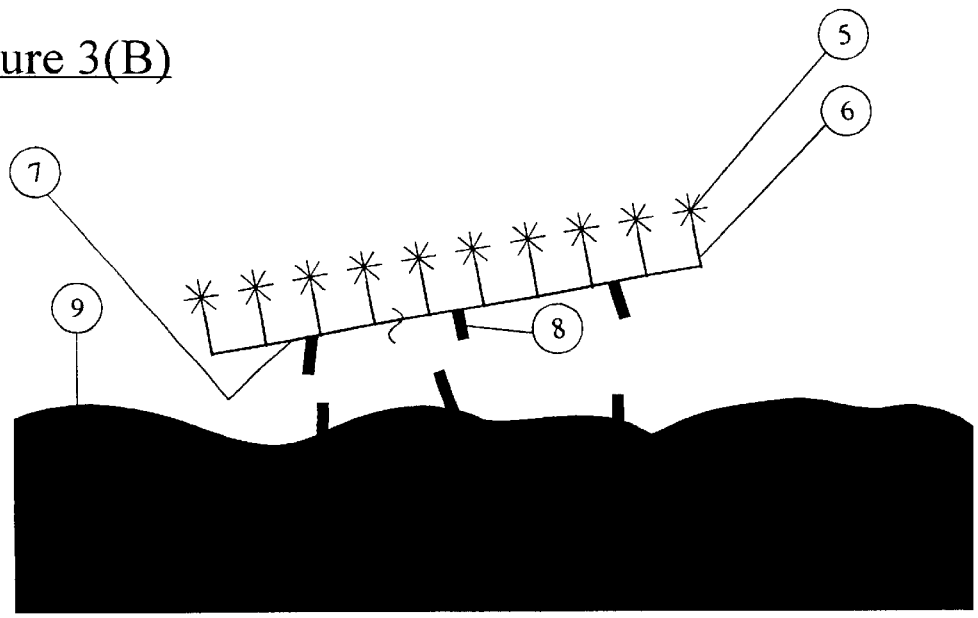
FIG. 3(B) schematically illustrates one or several tracers (5) being released from the formation (9) as a result of a chemical reaction leading to the breakage of link (8) between the link (7) and the surface (9).
Figure 6:
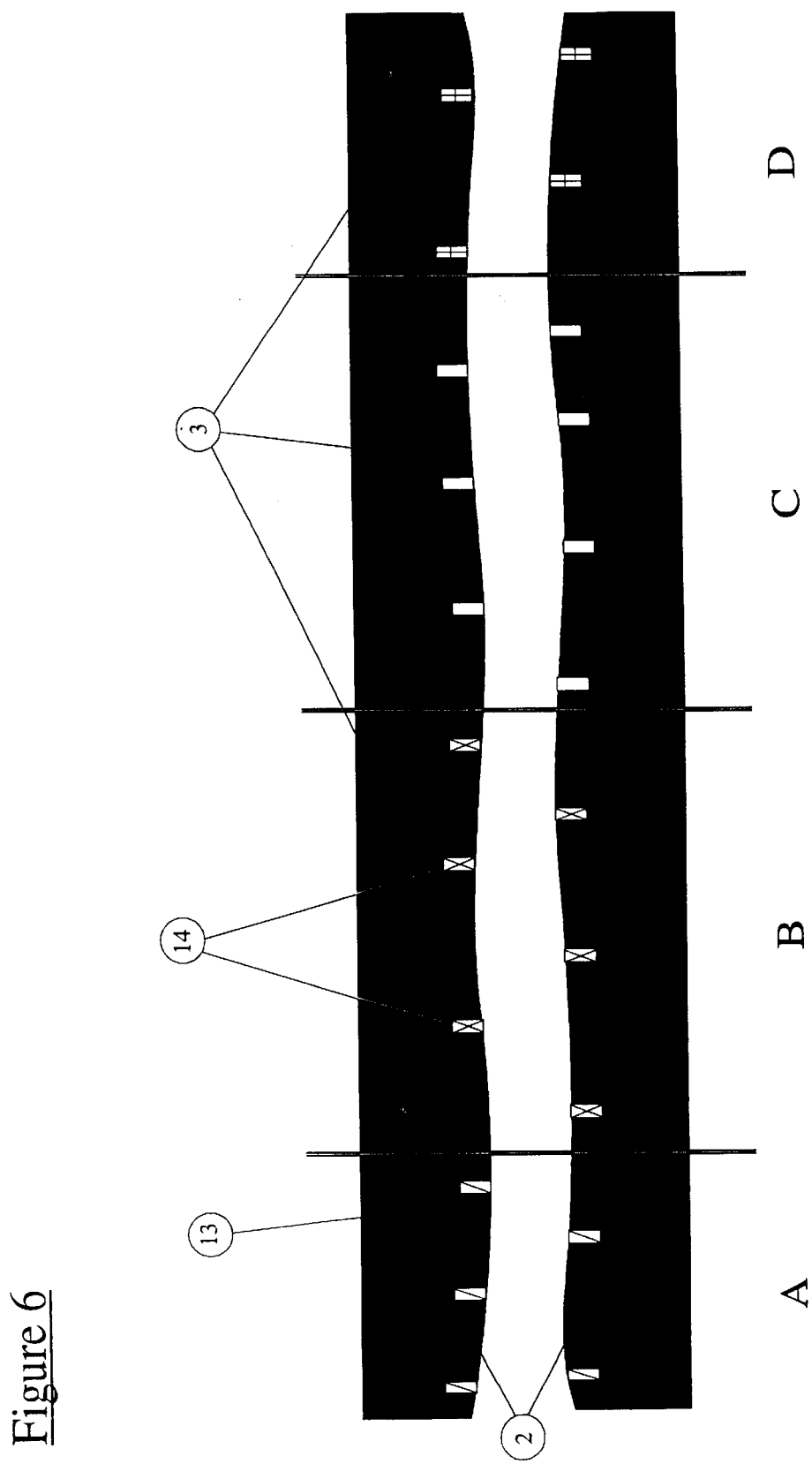
FIGS. 6 and 7 schematically illustrate different ways of locating tracer packages in various zones/sections along the well in a reservoir formation. The tracers are e.g. placed along the well with a certain pattern or injected into the formation, e.g. as swellable porous or solid polymer matrixes.
Figure 7:
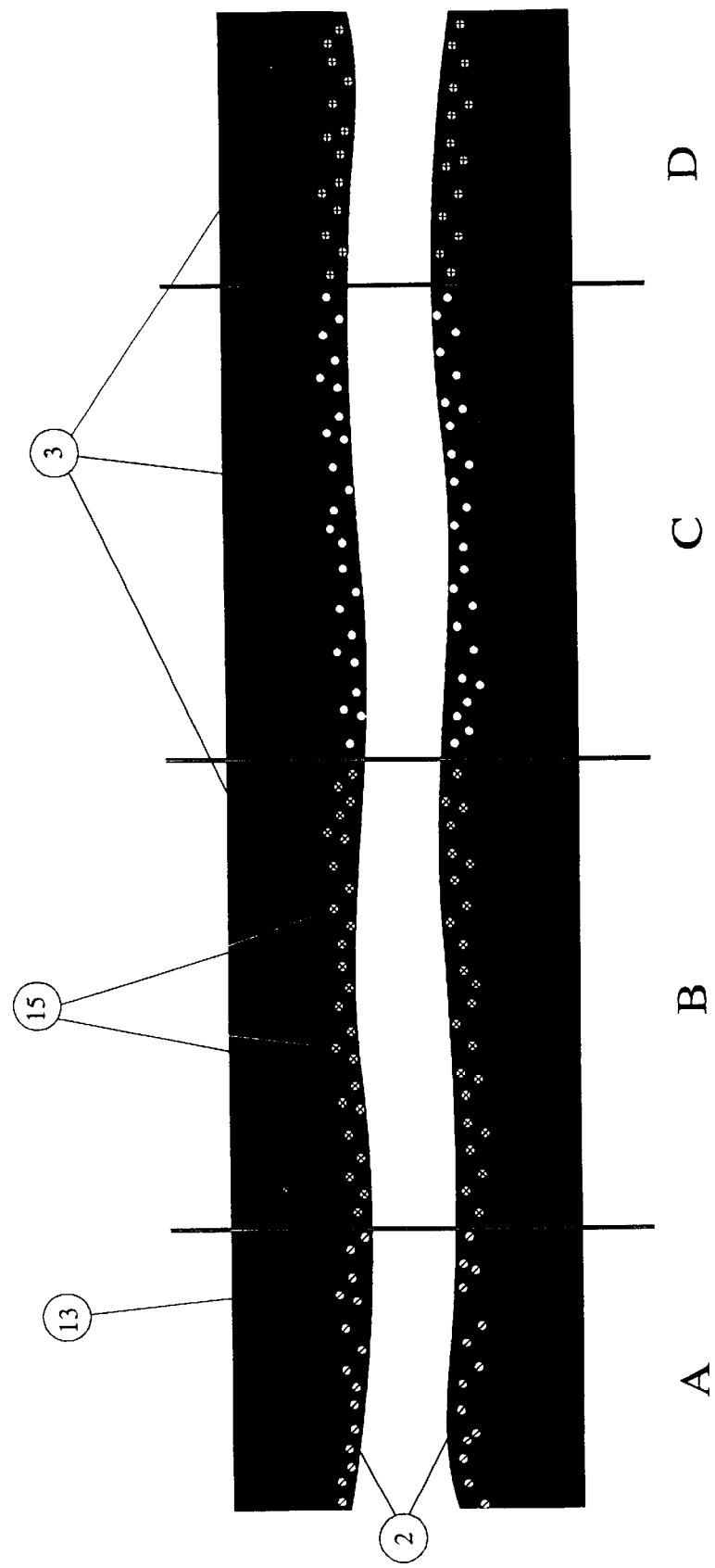
Figure 8:
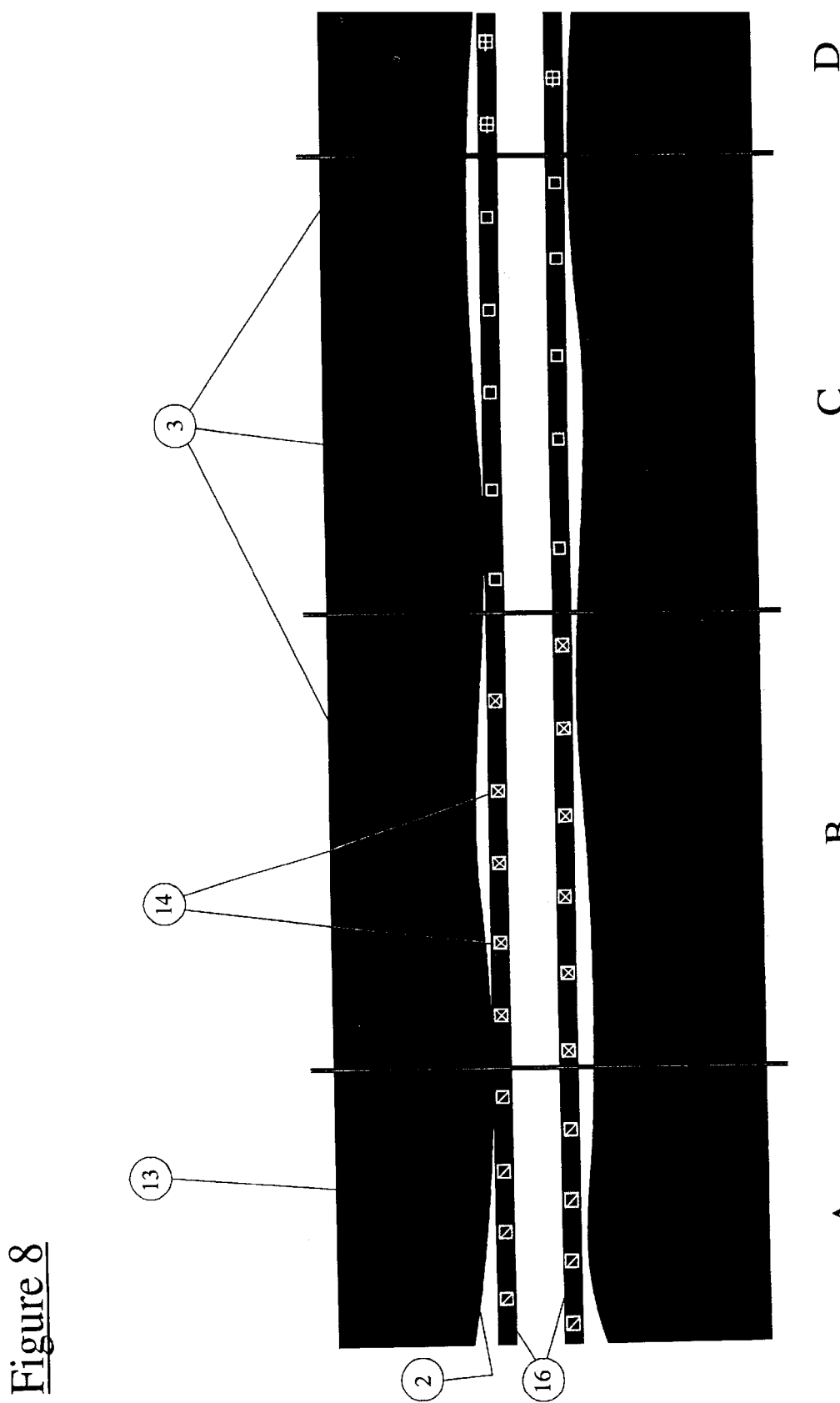
FIG. 8 schematically illustrates locating tracer packages in various zones/sections along the well in the constructions or filters around the well. The tracers are e.g. placed along the well with certain patterns, injected into the constructions or filters around the well, mixed with the material in the filter content, or fixed on the constructions or filters around the well.

FIG. 9 is a schematic illustration of a method for selection of desired emission spectra for detection of individual tracer particles with different spectra using optical filters. (I) shows whole spectra of the reflected and emitted lights from the carrying fluid and tracer particles A–D, together with the emission spectrum for the laser. The different tracer particles A–D may initially be arranged in the well as illustrated in FIG. 1. The reflected light from the light source (laser) and the fluorescent light from the various tracer particles A–D may be separated using proper optical filter combinations, such that only the light from a certain tracer particle group is converted to electric signals. In FIG. 9 optical bandpass filters block the unwanted light spectra and transmit the desired light spectra as illustrated in (II)–(V). The electric signals from each detector are amplified and converted separately and finally recorded on a file or displayed on the monitor of a computer. The choice of fluorescent tracer particles or chemicals and optical filter combination is based on light spectral analyses. Using this technique, the obtained signals from passage of each tracer particle group is similar to those from a single particle group and can be treated the same. By this technique it is possible to monitor the reservoir dynamics and detect all tracer groups from various well sections simultaneously.

7. Experiments with Oil Reservoir Simulation System

A simple column filled with glass beads (2–3 mm) was set up. The column had the dimensions as follows, length 11.5 cm, diameter 5.5 cm and a total volume of 273 $cm^3$, of which most were taken up by the glass beads. A glass sinter fixed in the bottom of the column acted as a bed for the beads and even the flow of liquid. A peristaltic pump was placed at the lower end of the column, and a drain was placed at the top. The arrangement made it possible to fill the column from the bottom with no air bubbles trapped.

The pump could run in both directions, thus enabling flows from both the bottom and up and also a flow from the top and down. The density of the liquids sets the direction of the flow. For water to replace oil the flow is from bottom and up, but for oil to replace the water the flow is from top and downwards, both to ensure a plug flow.

An initial goal with this set-up was to demonstrate the possibility of detecting a change from one phase to the other. When the column is filled with oil, it is important to detect that the water coming out have been passing through a certain volume or part of the column. A water soluble, but not oil soluble, tracer was then placed at a point in the bulk of the beads. This tracer was strongly colored making a visual detection easy.

Detection of Water Passing through Tracer Experiment Above

Initially the column was filled with oil and there was no color whatsoever in the liquid. Clear liquid was coming from the top of the column. The inflow at the bottom changed to water and water replaced the oil from beneath. This is typically a plug flow. At some point the water hit the point in the bead packing where the colored tracer was placed (Methylthymol Blue, water soluble), typically a few milligrams. At this point the water phase changed its color from transparent to blue in this case which is apparent from the picture reproduced. The experiment demonstrated that the water phase passed through a known fixed point in the column and that this could be monitored.

The visual detection of a colored dye is not a very sensible technique and more sensible techniques were tested. By using a fluorescent dye and using ultra violet light to trigger the fluorescence, a far more sensible system was achieved. Not only was visual detection by eyes possible, but also the use of a spectrometer in conjunction with an ultra violet source. The detection limits reachable with this technique is low enough to utilize this method in simulated oil well structures. The experiment was performed by placing a small amount (typically a few milligrams) in the glass bead packing. A UV lamp at 265 nm was placed in the vicinity of the column and the fluorescent dye started to emit visible light when exposed to the UV radiation. At present no instrumental detection is needed since the fluorescent light emitted by the dye is strong enough to be visible to the naked eye. This experiment demonstrated the principle that water flowing through a known fixed location in the column can be detected and monitored. It also demonstrated that a fluorescent dye is a very powerful technique for this kind of monitoring.

Detection of Oil Passing through the Tracer Experiment Above

Initially the column was filled with water and there was no color whatsoever in the water. Clear water was coming from the top of the column. The flow was then reversed and oil drawn from the top and down the column by means of a reversed flow of the peristaltic pump. The oil replaced the water from above, thus yielding a plug flow. At some point the oil phase hit the tracer, in this case a dye that was only soluble in oil and not in water (Oil Blue N), typically a few milligrams. The oil that had passed through this dye was strongly colored and could easily be detected visually.. This experiment demonstrated that an oil phase that has passed through a fixed known point in the column can be detected, in this case with a colored dye.

Sensitivity of Tracers

For this simple and easy experiment only dye tracers were used. However, to achieve the sensitivity needed for real experiments very different tracers must be used. Fluorocarbon compounds yield an extremely high sensitivity in the electron capture detector, and a combination of a suitable fluorocarbon and GC/ECD is a known and well suited technique for this kind of purpose. The use of fluorocarbons in oil well monitoring is a well-established method in the oil industry.

Environmental Impact of PerFluoroCarbons

The perfluorocarbons have a large global warming potential. The environmental impact of these compounds will cause these kinds of molecules to be phased out. It is therefore of interest to look for tracers that are environmentally acceptable, e.g. have no ozone depletion potential and a very low or zero GWP. At the same time maintaining the wanted properties of the tracers, like good chemical stability and a very high sensitivity with respect to the electron capture detector and negative ion chemical ionization mass spectrometry, NCI-MS.

The new class of compound developed as replacements for CFSs namely the Perfluoroethers (of which an example is CHF2—O—CF2—O—CHF2) is a very good and environmentally acceptable alternative to the fluorocarbons. These compounds exist with very different chain lengths thereby yielding a lot of different trace molecules to be used. These ethers are also slightly water soluble making them easy to detect in the water phase.

Dye in Water Soluble Matrix

Dissolving 20 g Polyvinylpyrrolidine K90 in 80 g of water with magnetic stirring close to the boiling point made a water soluble matrix. A few mg of water soluble methylthymol blue was added, and the solution was brought to room temperature. The brownish/yellow transparent and viscous liquid was kept at 50° C. for 48 hours. The resulting solid polymer was broken to pieces and used in the experiments. A piece of the material was placed in water, and another one in transparent oil. The piece in the water phase dissolved, giving a blue transparent solution. Nothing happened in the oil phase. The tracer containing polyvinylpyrrolidine matrix was placed in the elluation column as described above, and elluted from below with an lamp oil. The tracer was stable under these conditions. The elluent was then exchanged to water. The tracer containing matrix began to dissolve when the water reached this level in the column, and the matrix started to dissolve releasing the tracer color. The release of the tracer was much slower compared to the pure dye above.

Having described preferred embodiments of the invention it will be apparent to those skilled in the art that other embodiments incorporating the concepts may be used. These and other examples of the invention illustrated above are intended by way of example only and the actual scope of the invention is to be determined from the following claims.

What is claimed is:

1. A method of monitoring hydrocarbon and water production from different production zones/sections in a hydrocarbon reservoir and/or injection wells and detection of different phenomena, the method comprising:

dividing regions around wells in the reservoir into a number of zones/sections;

injecting or placing specific tracers with unique characteristics for each zone/section into a formation in these regions such that the tracers are placed as integrated parts of the well completion or placed and immobilized in these regions through injection, squeeze or by other techniques, or the tracers can be immobilized or placed on a filter, a casing or constructions surrounding the well in each zone/section, the tracers being specific or introduced to provide specific information from each zone/section;

chemically immobilizing or integrating the tracers in the formation, constructions or filters around the wells, the tracers being chemically intelligent and released as a function of specific events;

immobilizing or integrating the tracers by using a polymer designed to adhere to the formation, the constructions or the filters, wherein the tracers are covalently linked or linked by ionic interactions to the polymers, and the tracers can also be contained in the polymer matrix; and detecting the tracers downstream so as to provide information about the various zones/sections.

2. The method according to claim 1, further comprising using fluid intelligent tracers, the tracers being released upon contact with either an oil, gas or water flow.

3. The method according to claim 2, further comprising using various perfluorinated hydrocarbons encapsulated in polymer matrixes or particles, the matrixes or particles being sensitive to water and hydrocarbon, respectively, as fluid intelligent tracers.

4. The method according to claim 1, further comprising releasing the tracers from the polymer by breaking the binding between the polymer and the tracer.

5. The method according to claim 1, further comprising releasing the tracers by degradation of the polymer, resulting in small oligomers or chemicals containing tracers in the production stream.

6. The method according to claim 1, further comprising controlling the degradation of polymer particles by using specially defined cross-linkers, the cross-linkers being modified so as to be sensitive towards specific events.

7. The method according to claim 6, wherein the specific events include pH, temperature, water or special chemicals added to the zones/sections.

8. The method according to claim 1, wherein the tracer is an oligonucleotide with special functional groups.

9. The method according to claim 1, further comprising performing short time and/or long time monitoring of the various zones/sections in the hydrocarbon reservoir by using a first group of tracers and a second group of tracers, wherein the first group of tracers are released over a short period of time and the second group of tracers are released gradually over a long period of time.

10. The method according to claim 1, further comprising monitoring sudden events occurring in the various zones/sections in the hydrocarbon reservoir by using tracers, the tracers being released suddenly in response to changes in the local surroundings of the tracer.

11. The method according to claim 1, wherein the tracers comprise fluorescent, phosphorescent, magnetic particles or fluids, colored particles, DNA or microorganisms.

12. The method according to claim 1, further comprising isolating and/or detecting the tracers by optical, spectroscopic, chromatographic, acoustic, magnetic, capacitive, PCR or microwave techniques, or by any combination of these techniques.

13. The method according to claim 1, wherein the different phenomena, which are detected, include local variations in pH, salinity, hydrocarbon composition, temperature, pressure, microorganisms, and a difference between production of formation and/or injection water from the various zones/sections.

14. A method of monitoring hydrocarbon and water production from different production zones/sections in a hydrocarbon reservoir and/or injection wells and detection of different phenomena, the method comprising:

dividing regions around wells in the reservoir into a number of zones/sections;

injecting or placing specific tracers with unique characteristics for each zone/section into a formation in these regions such that the tracers are placed as integrated parts of the well completion or placed and immobilized in these regions through injection, squeeze or by other techniques, or the tracers can be immobilized or placed on a filter, a casing or constructions surrounding the well in each zone/section, the tracers being specific or introduced to provide specific information from each zone/section;

chemically immobilizing or integrating the tracers in the formation or constructions or filters around the wells, the tracers being chemically intelligent and released as a function of specific events;

injecting specific triggers into the formation through the injection system triggering the release of tracers; and detecting the tracers downstream so as to provide information about the various zones/sections.

15. A method of monitoring hydrocarbon and water production from different production zones/sections in a hydrocarbon reservoir and/or injection wells and detection of different phenomena, the method comprising:

dividing regions around wells in the reservoir into a number of zones/sections;

injecting or placing specific tracers with unique characteristics for each zone/section into a formation in these regions such that the tracers are placed as integrated parts of the well completion or placed and immobilized in these regions through injection, squeeze or by other techniques, or the tracers can be immobilized or placed on a filter, a casing or constructions surrounding the well in each zone/section, the tracers being specific or introduced to provide specific information from each zone/section;

chemically immobilizing or integrating the tracers in the formation or constructions or filters around the wells, the tracers being chemically intelligent and released as a function of specific events;

detecting the tracers downstream so as to provide information about the various zones/sections; and detecting the presence of microorganisms in the different zones/sections by using different fluorogenic and/or chromogenic enzyme substrates as tracers, the substrates and the fluorogenic/chromogenic part being cleaved by extracellular enzymes produced by the microorganisms in the reservoir.

* * * * *